(12) United States Patent
Yamamoto et al.

(10) Patent No.: US 6,187,046 B1
(45) Date of Patent: Feb. 13, 2001

(54) PROSTHETIC BONE MATERIAL AND PROCESS FOR THE PRODUCTION OF THE SAME

(75) Inventors: Akira Yamamoto; Masanori Nakasu, both of Tokyo; Yoshie Tominaga, Saitama-ken, all of (JP)

(73) Assignee: Asahi Kogaku Kogyo Kabushiki Kaisha, Tokyo (JP)

( * ) Notice: Under 35 U.S.C. 154(b), the term of this patent shall be extended for 0 days.

(21) Appl. No.: 09/042,087

(22) Filed: Mar. 13, 1998

(30) Foreign Application Priority Data

Mar. 14, 1997 (JP) .................................................. 9-060567
Oct. 13, 1997 (JP) .................................................. 9-278757

(51) Int. Cl.$^7$ ...................................................... A61F 2/28
(52) U.S. Cl. ................................... 623/16.11; 623/18.11; 623/23.36; 623/23.48; 623/23.61
(58) Field of Search .................................. 623/16, 16.11, 623/18.11, 23.36, 23.48, 23.61

(56) References Cited

U.S. PATENT DOCUMENTS

| | | |
|---|---|---|
| 4,113,500 | 9/1978 | Ebihara et al. . |
| 4,149,893 | 4/1979 | Aoki et al. . |
| 4,149,894 | 4/1979 | Ebihara et al. . |
| 4,778,471 | 10/1988 | Bajpai . |
| 4,798,585 | 1/1989 | Inoue et al. . |
| 4,846,828 * | 7/1989 | Takai et al. ............................ 604/387 |
| 4,846,838 | 7/1989 | Takai et al. . |
| 4,897,250 | 1/1990 | Sumita . |
| 4,904,257 | 2/1990 | Mori et al. . |
| 4,919,751 | 4/1990 | Sumita et al. . |
| 4,957,674 | 9/1990 | Ichitsuka et al. . |
| 4,969,913 | 11/1990 | Ojima . |
| 5,017,518 | 5/1991 | Hirayama et al. . |
| 5,064,436 | 11/1991 | Ogiso et al. . |
| 5,082,803 | 1/1992 | Sumita . |
| 5,084,050 | 1/1992 | Draenert . |
| 5,134,009 * | 7/1992 | Ichituka et al. ...................... 423/113 |
| 5,137,534 | 8/1992 | Sumita . |
| 5,147,361 | 9/1992 | Ojima et al. . |
| 5,149,368 | 9/1992 | Liu et al. . |
| 5,171,720 | 12/1992 | Kawakami . |
| 5,180,426 | 1/1993 | Sumita . |
| 5,215,941 | 6/1993 | Yasukawa . |
| 5,240,659 | 8/1993 | Ichitsuka et al. . |
| 5,522,894 * | 6/1996 | Draenert ................................. 623/16 |
| 5,531,794 * | 7/1996 | Takagi et al. ........................... 623/16 |

FOREIGN PATENT DOCUMENTS

| | | |
|---|---|---|
| 0359278 | 3/1990 | (EP) . |
| 0577342 | 1/1994 | (EP) . |
| 2237564 | 5/1991 | (GB) . |
| 62-12680 | 1/1987 | (JP) . |
| 87/04110 | 7/1987 | (WO) . |

OTHER PUBLICATIONS

Copy of a United Kingdom Search Report dated May 22, 1998.
Derwent Abstract No. 93–239294.
Database WPI, Section Ch, Week, 9330, Derwent Publications Ltd., London, GB, An 93–239294, XP002101252.
Patent Abstracts of Japan, vol. 013, No. 556 (C–664), Dec. 11, 1989.
Patent Abstracts of Japan, vol. 095, No. 11, Dec. 26, 1995.

* cited by examiner

Primary Examiner—Michael J. Milano
Assistant Examiner—Hieu Phan
(74) Attorney, Agent, or Firm—Greenblum & Bernstein P.L.C.

(57) ABSTRACT

A prosthetic bone material comprising a bonded and sintered product of granules of calcium phosphate compound having a particle size of at least 100 $\mu$m, each of the granules being bonded with particulates of calcium phosphate compound having a particle size of about 1 to 40 $\mu$m, in which the granules are bonded to each other while retaining their original shape, and their bonding strength is a level sufficient to maintain their own shape when the bonded and sintered product is disintegrated, produced by mixing the granules and the particulates, followed by firing the mixture at a temperature of about 800 to 1,200° C.

12 Claims, No Drawings

PROSTHETIC BONE MATERIAL AND PROCESS FOR THE PRODUCTION OF THE SAME

BACKGROUND OF THE INVENTION

1. Field of the Invention

The present invention relates to a prosthetic bone material, i.e., a prosthetic material to be embedded in a lacking portion of the bone, and its production process. More particularly, the present invention relates to a calcium phosphate-based prosthetic bone material having a block-like shape as an original state and capable of changing its shape into granules when the prosthetic bone material is embedded into a lacking portion of the bone during a surgical operation, thereby ensuring the ease of shaping the material. The present invention also relates to a process for the production of such prosthetic bone material.

2. Description of the Related Art

Hitherto, granular calcium phosphate-based prosthetic bone materials have been developed and are commercially available. However, since the prosthetic bone materials are in the form of granules, when they are actually embedded into a lacking portion of the bone during a surgical operation, a problem arises with the granules scattering around unnecessary portions of the bone.

Furthermore, the use of block-shaped prosthetic bone materials makes the shaping of the block in conformity with the configuration of the lacking portion of the bone troublesome upon surgery.

SUMMARY OF THE INVENTION

It is therefore an object of the present invention to solve the above-described related art problems by providing a calcium phosphate-based prosthetic bone material having bonded granules of calcium phosphate compound, the material having a shape that is retained until the material is separated under pressure.

Another object of the present invention is to provide a production process suitable for the production of the prosthetic bone material according to the present invention.

The present invention is based on the findings that the above objects can be accomplished if the granules of calcium phosphate compound are bonded and sintered to each other to make a block-shaped product, while retaining their shape as granules, so that the resulting product may be easily handled and can be easily disintegrated and separated via the application of hand-pressure or the like (1–50 kg/cm$^2$) into granules, when the product is embedded in a lacking portion of the bone at the scene of surgical operation. The granules after disintegration have or substantially have the same size and shape as the granules in the block-shaped object. Preferably, the size and shape of the granules do not change during disintegration and separation.

That is, in one aspect of the present invention, there is provided a prosthetic bone material comprising a bonded and sintered product of granules of calcium phosphate compound having a particle size of at least about 100 μm, each of the granules being bonded with particulates of calcium phosphate compound having a particle size of about 1 to 40 μm, in which the granules are bonded to each other while retaining their original shape, and the granules have a bonding strength that is at a level sufficient to maintain or substantially maintain the size and shape of the granules when the bonded and sintered product is disintegrated.

In another aspect of the present invention, there is provided a process for the production of a prosthetic bone material which includes: mixing granules of calcium phosphate compound having a particle size of at least about 100 μm with particulates of calcium phosphate compound having a particle size of about 1 to 40 μm, and firing the mixture at a temperature of about 800 to 1,200° C.

In yet another aspect of the present invention, there is provided a process for the production of a prosthetic bone material which includes: mixing granules of calcium phosphate compound having a particle size of at least about 100 μm with particulates of calcium phosphate compound having a particle size of about 1 to 40 μm, adding to the mixture an aqueous solution of dispersing agent and/or binding agent capable of being dissipated during firing, and, after molding and drying, firing the molded and dried product at a temperature of about 800 to 1,200° C.

The present disclosure relates to subject matter contained in Japanese Patent Application No. 09-60567 (filed on Mar. 14, 1997) and No. 09-278757 (filed on Oct. 13, 1997) which are expressly incorporated herein by reference in their entireties.

DESCRIPTION OF THE PREFERRED EMBODIMENTS

As described above, the prosthetic bone material according to the present invention is basically composed of a bonded product of granular calcium phosphate compound having a particle size of at least about 100 μm, and in this bonded product, the granules are bonded to each other under the condition of retaining their original shape and at a bonding strength which is sufficient to be easily disintegrated with the pushing pressure of a human finger or the like (1–50 kg/cm$^2$) and, after disintegration, is able to maintain or substantially maintain the shape of granules. The bonding of the granules to each other relies upon the aid of the particulates of calcium phosphate compound having a particle size of about 1 to 40 μm.

The calcium phosphate compound used herein can comprise a single calcium phosphate compound or a mixture of calcium phosphate compounds. For example, the calcium phosphate compound can have a molar Ca/P ratio of 1.0 to 2.0, and can comprise, for example, hydroxyapatite, fluoroapatite, calcium hydrogenphosphate, tricalcium phosphate, tetracalcium phosphate and other calcium phosphates. The most preferred calcium phosphate compound includes hydroxyapatite as a principal component thereof.

The particle size of the granules of calcium phosphate compound is not specifically restricted as long as it is included in the scope of the definition "granular prosthetic bone material" and is generally about 100 μm or more, and an upper limit of about 5000 μm.

Further, the granules of calcium phosphate compound may be either dense (having a porosity of 0%) or porous (having a porosity of up to 60%), and they may be produced in any manner, such as by using any conventional production methods. Moreover, the granules of calcium phosphate compound can have any shape. Preferably, the granular calcium phosphate compound has a spherical shape.

From only granules of calcium phosphate compound having a particle size of at least about 100 μm, it is difficult to produce, upon sintering the granules, a bonded product in which the granules simply contact each other. Contrary to this, according to the present invention, to aid the bonding of the granules, particulates of calcium phosphate compound are added to the granules of calcium phosphate compound. Because they can be easily sintered in comparison with the granular calcium phosphate compound, in the sintering process, the particulates of calcium phosphate compound can significantly contribute to an improved bonding of the granules as a function of the sintering of the particulates themselves. The particulates of calcium phosphate compound that enables the aiding of bonding of the granules of calcium phosphate compound can be of any size smaller than that of the granules of calcium phosphate compound. Preferably, the particulates of calcium phosphate compound have a particle size in the range of about 1 to 40 μm. Particle sizes above or below the above range will not ensure the function of the particulates as a bonding aid, that is, it will only show an insufficient binding effect.

As in the production of the granules of calcium phosphate compound, the particulates of calcium phosphate compound may be produced in any manner, such as by using any conventional production methods.

In addition, it is preferred in the prosthetic bone material of the present invention that the granules of calcium phosphate compound having a particle size of at least about 100 μm and the particulates of calcium phosphate compound having a particle size of about 1 to 40 μm are contained in a ratio by weight of about 1:0.1 to 1:1. If the particulates are used in a lesser amount, they can not ensure their binding effect, and if they are used in an amount above 1:1, the granules can not retain their own shape, because a sintering strength of the granules is increased.

The prosthetic bone material of the present invention can be produced by mixing the granules of calcium phosphate compound having a particle size of at least about 100 μm with the particulates of calcium phosphate compound having a particle size of about 1 to 40 μm, followed by firing the resulting mixture at a temperature of about 800 to 1,200° C.

In the production process of the present invention, the granules can be mixed with the particulates as a binder either wherein each of the granules and particulates are dry, or in which either or both of the granules and particulates are in a wet form. For example, the granules and/or particulates can be used as an aqueous suspension, however, to obtain an improved bonding of the granules after sintering, it is preferred that the granules and the particulates are mixed after they are suspended in water, because the particulates can effectively adhere to the granules. Further, when the granules and the particulates are mixed after they are suspended in water, it is preferred to add a dispersing agent capable of being dissipated during the firing of the mixture as an aqueous suspension to assist in a uniform dispersion of the granules and the particulates in the suspension, thereby ensuring the production of a more uniformly bonded prosthetic bone material. Various materials can be utilized as the dispersing agent, such as lower alcohols including, for example, ethanol and isopropyl alcohol. Preferably, the dispersing agent is added to the mixture in an amount of about 1.5 times or more of the total weight of the granules and particulates.

Additionally, in the production process of the present invention, the granules and particulates may be mixed after addition of an aqueous solution of a binding agent capable of being dissipated during firing. When a binding agent is not present, removal of the charged mixture from the mold prior to sintering is not ensured. In contrast, if a binding agent is added to the mixture and the resulting aqueous suspension is charged into and dried (at 80° C.) in a mold, the dried product can be removed from the mold prior to sintering of the same. In particular, the binding agent provides an improved moldability of the product, because the strength of bonding between granules is increased to give mechanical strength to the dried product.

As the binding agent capable of being dissipated during firing, cellulose derivatives such as methyl cellulose and the like, polysaccharides such as curdlan and the like, and synthetic polymers such as polyvinyl alcohol, polyacrylic acid, polyacrylamide, polyvinyl pyrrolidone and the like, may be used.

After the granules, the particulates and an aqueous solution of the binding agent are mixed, and the mixture is charged in a mold, it is generally preferred that the content of the mold is heated and dried at a temperature of about 50 to 120° C.

With regard to the binding agent, it is preferred that the agent be used at a concentration of about 0.1 to 10.0%, and is added in an amount of about 10 to 80% based on the total weight of the granules and the particulates. It is not preferred to use the binding agent in a concentration out of the above-described range because concentration below 0.1% does not ensure a binding effect, and concentration above 10.0% shows an excessively increased viscosity and thus a deteriorated flowability, thereby causing difficulty in uniform mixing of the granules and particulates. Similarly, it is not preferred to use the binding agent in an amount out of the above-described range, because an amount below 10% does not ensure an effect as a binder, and an amount above 80% results in a precipitation of the granules, thereby causing difficulty in uniform mixing of the granules with the particulates.

In addition, in the production process of the present invention, both the above-described dispersing agent and binding agent may be added to a mixture of the granules and the particulates.

In the practice of the present invention, the granules of calcium phosphate compound useful in the production of the bonded product, can include unfired granules or fired granules. When unfired granules are used, shrinkage of the granules occurs during sintering; whereas, when fired granules are used, shrinkage is avoided because the granules have already been fired once, and therefore (the use of fired granules) enables the carrying out of molding in the stage just before the final firing step. However, when unfired granules are used, there is an advantage that only one firing step is sufficient to complete the production process.

In the production process of the present invention, firing is preferably carried out at a temperature of about 800 to 1,200° C. A firing temperature below 800° C. can result in a product having an excessively low sintering strength and thus a high possibility of being broken, thereby causing difficulty in handling the resulting prosthetic bone material. Further, a firing temperature above 1,200° C. can result in a product having an excessively high sintering strength which prevents the resulting prosthetic bone material from disintegrating into the original granules when the bone material is embedded into a bone-lacking portion during an operation. That is, it would be difficult to shape the produced prosthetic bone material in conformity with the configuration of the bone-lacking portion to be repaired, and thus, would not satisfy the requirements of the present invention.

The bonded product of the granular calcium phosphate compound obtained according to the production process of the present invention, due to the granular compound having a very large particle size, has a structure so that the granules are bonded to each other by very few contact points, while retaining the shape of granules. The mechanical strength of the bonded product is such a level that the bonded product can be easily disintegrated when it is pressurized by the force of a human finger and the like, but, even after disintegration of the bonded product, the granules can retain their original shape.

EXAMPLES

The present invention will be further described with reference to its working examples. Note, however, that the present invention should not be restricted to these examples.

Example 1

Hydroxyapatite powder was compressed in a tablet machine, and then milled in a mortar. The milled powder was further granulated to obtain unfired hydroxyapatite granules having a particle size of 100 to 400 $\mu$m. To 1 g of the thus obtained hydroxyapatite granules, 0.5 g of unfired hydroxyapatite powder having an average particle size of 3 $\mu$m was added, and the mixture was fired at 1,200° C. for 4 hours. It was observed in the fired product that the hydroxyapatite granules were bonded to each other while retaining their original shape.

Example 2

400 g of an aqueous 1 wt. % solution of methyl cellulose was stirred in a mixer to make bubbles therein. Then, 200 g of hydroxyapatite powder consisting of spherical powders of hydroxyapatite having an average particle size of 10 $\mu$m and fine hydroxyapatite powder having an average particle size of 1 $\mu$m (hereinafter, the mixed powder will be referred to as "hydroxyapatite powder") were added to the bubbled solution of methyl cellulose, followed by mixing. The mixture was dried at 80° C. for 36 hours. The dried product was milled in a mortar, and further granulated to obtain unfired porous hydroxyapatite granules having a particle size of 100 to 400 $\mu$m and a porosity of 20%. Added to 1 g of thus obtained hydroxyapatite granules was 0.5 g of unfired hydroxyapatite powder having an average particle size of 3 $\mu$m, and the mixture was fired at 1,200° C. for 4 hours. It was observed in the fired product that the hydroxyapatite granules were bonded to each other while retaining their original shape.

Example 3

400 g of an aqueous 1 wt. % solution of methyl cellulose was stirred in a mixer to make bubbles therein. Then, 200 g of tricalcium phosphate powder consisting of spherical powders of tricalcium phosphate having an average particle size of 10 $\mu$m and fine tricalcium phosphate powder having an average particle size of 1 $\mu$m (hereinafter, the mixed powder will be referred to as "tricalcium phosphate powder") were added to the bubbled solution of methyl cellulose, followed by mixing. The mixture was set in a drier at 80° C. and dried for 36 hours. The dried product was milled in a mortar, and further granulated to obtain unfired porous tricalcium phosphate granules having a particle size of 100 to 400 $\mu$m and a porosity of about 20%. Added to 1 g of the thus obtained tricalcium phosphate granules was 0.5 g of unfired tricalcium phosphate powder having an average particle size of 3 $\mu$m, and the mixture was fired at 1,200° C. for 4 hours. It was observed in the fired product that the tricalcium phosphate granules were bonded to each other while retaining their original shape.

Example 4

Hydroxyapatite powder was charged in a mold made of DERLIN(trade mark) (manufactured from polyformalehyde), and pressurized in a hydraulic press to obtain a compact powder. The compact powder was contained in a pouch of vinyl film, vacuum packed, and subjected to a pressure of 2,000 kg/cm$^2$ in a hydrostatic press. The compact powder was milled in a mortar, and further granulated to obtain unfired dense hydroxyapatite granules having a particle size of 100 to 400 $\mu$m. Added to 1 g of the thus obtained hydroxyapatite granules was 0.5 g of unfired hydroxyapatite powder having an average particle size of 3 $\mu$m, and the mixture was fired at 1,200° C. for 4 hours. It was observed in the fired product that the hydroxyapatite granules were bonded to each other while retaining their original shape.

Example 5

Tricalcium phosphate powder was charged in a mold made of DERLIN(trade mark) (manufactured from polyformalehyde), and pressurized in a hydraulic press to obtain compact powder.

The compact powder was contained in a pouch of vinyl film, vacuum packed, and subjected to a pressure of 2,000 kg/cm$^2$ in a hydrostatic press. The compact powder was milled in a mortar, and granulated to obtain unfired dense tricalcium phosphate granules having a particle size of 100 to 400 $\mu$m. Added to 1 g of the thus obtained tricalcium phosphate granules was 0.5 g of unfired tricalcium phosphate powder having an average particle size of 3 $\mu$m, and the mixture was fired at 1,200° C. for 4 hours. It was observed in the fired product that the tricalcium phosphate granules were bonded to each other while retaining their original shape.

Example 6

The procedure of Example 1 was repeated to produce unfired hydroxyapatite granules having a particle size of 100 to 400 $\mu$m. Added to 1 g of the thus obtained hydroxyapatite granules was 1.0 g of unfired hydroxyapatite powder having an average particle size of 3 $\mu$m, and the mixture was fired at 1,200° C. for 4 hours. It was observed in the fired product that the hydroxyapatite granules were bonded to each other while retaining their original shape. The bonded product obtained in this example indicated a higher mechanical strength than that of Example 1.

Comparative Example 1

The procedure of Example 1 was repeated to produce unfired hydroxyapatite granules having a particle size of 100 to 400 $\mu$m. Added to 1 g of the thus obtained hydroxyapatite granules was 1.5 g of unfired hydroxyapatite powder having an average particle size of 3 $\mu$m, and the mixture was fired at 1,200° C. for 4 hours. It was observed in the fired product that the hydroxyapatite granules were bonded to each other. The bonded product obtained in this comparative example indicated a higher mechanical strength than that of Example 1, however, it could not retain an original shape of the granules, because the fine powders that were sintered were fused to the granular particles obtained upon disintegration of the bonded product due to an excessively increased amount of the fine powders used.

Comparative Example 2

The procedure of Example 2 was repeated to produce unfired porous hydroxyapatite granules having a particle size of 100 to 400 $\mu$m and a porosity of 20%. Added to 1 g of the thus obtained hydroxyapatite granules was 1.5 g of unfired hydroxyapatite powder having an average particle size of 3 μm, and the mixture was fired at 1,200° C. for 4 hours. It was observed in the fired product that the hydroxyapatite granules were bonded to each other. The bonded product obtained in this comparative example indicated a higher mechanical strength than that of Example 2, however, it could not retain an original shape of the granules, because the fine powders that were sintered were fused to the granular particles obtained upon disintegration of the bonded product due to an excessively increased amount of fine powders used.

Comparative Example 3

The procedure of Example 3 was repeated to produce unfired porous tricalcium phosphate granules having a particle size of 100 to 400 μm and a porosity of 20%. Added to 1 g of the thus obtained tricalcium phosphate granules was 1.5 g of unfired tricalcium phosphate powder having an average particle size of 3 μm, and the mixture was fired at 1,200° C. for 4 hours. It was observed in the fired product that the tricalcium phosphate granules bonded to each other. The bonded product obtained in this comparative example indicated a higher mechanical strength than that of Example 3, however, it could not retain an original shape of the granules, because the fine powders that were sintered were fused to the granular particles obtained upon disintegration of the bonded product due to an excessively increased amount of the fine powders used.

Comparative Example 4

The procedure of Example 4 was repeated to produce unfired dense hydroxyapatite granules having a particle size of 100 to 400 μm. Added to 1 g of the thus obtained hydroxyapatite granules was 1.5 g of unfired hydroxyapatite powder having an average particle size of 3 μm, and the mixture was fired at 1,200° C. for 4 hours. It was observed in the fired product that the hydroxyapatite granules were bonded to each other. The bonded product obtained in this comparative example indicated a higher mechanical strength than that of Example 4, however, it could not retain an original shape of the granules, because the fine powders that were sintered were fused to the granular particles obtained upon disintegration of the bonded product due to an excessively increased amount of the fine powders used.

Comparative Example 5

The procedure of Example 5 was repeated to produce unfired dense tricalcium phosphate granules having a particle size of 100 to 400 μm. Added to 1 g of the thus obtained tricalcium phosphate granules, added was 1.5 g of unfired tricalcium phosphate powder having an average particle size of 3 μm, and the mixture was fired at 1,200° C. for 4 hours. It was observed in the fired product that the tricalcium phosphate granules bonded to each other. The bonded product obtained in this comparative example indicated a higher mechanical strength than that of Example 5, however, it could not retain an original shape of the granules, because the fine powders that were sintered were fused to the granular particles obtained upon disintegration of the bonded product due to an excessively increased amount of fine powders used.

Example 7

The procedure of Example 1 was repeated to produce unfired hydroxyapatite granules having a particle size of 100 to 400 μm. Added to 1 g of the thus obtained hydroxyapatite granules was 0.5 g of unfired hydroxyapatite powder having an average particle size of 40 μm, and the mixture was fired at 1,200° C. for 4 hours. It was observed in the fired product that the hydroxyapatite granules were bonded to each other while retaining their original shape. The bonded product obtained in this example indicated a lower mechanical strength than that of Example 1.

Example 8

The procedure of Example 2 was repeated to produce unfired porous hydroxyapatite granules having a particle size of 100 to 400 μm and a porosity of 20%. Added to 1 g of the thus obtained hydroxyapatite granules was 0.5 g of unfired hydroxyapatite powder having an average particle size of 40 μm, and the mixture was fired at 1,200° C. for 4 hours. It was observed in the fired product that the hydroxyapatite granules were bonded to each other while retaining their original shape.

Example 9

The procedure of Example 3 was repeated to produce unfired porous tricalcium phosphate granules having a particle size of 100 to 400 μm and a porosity of 20%. To 1 g of the thus obtained tricalcium phosphate granules, added was 0.5 g of unfired tricalcium phosphate powder having an average particle size of 40 μm, and the mixture was fired at 1,200° C. for 4 hours. It was observed in the fired product that the tricalcium phosphate granules were bonded to each other while retaining their original shape.

Example 10

The procedure of Example 4 was repeated to produce unfired dense hydroxyapatite granules having a particle size of 100 to 40 μm. Added to 1 g of the thus obtained hydroxyapatite granules was 0.5 g of unfired hydroxyapatite powder having an average particle size of 40 μm, and the mixture was fired at 1,200° C. for 4 hours. It was observed in the fired product that the hydroxyapatite granules were bonded to each other while retaining their original shape.

Example 11

The procedure of Example 5 was repeated to produce unfired dense tricalcium phosphate granules having a particle size of 100 to 400 μm. Added to 1 g of the thus obtained tricalcium phosphate granules was 0.5 g of unfired tricalcium phosphate powder having an average particle size of 40 μm, and the mixture was fired at 1,200° C. for 4 hours. It was observed in the fired product that the tricalcium phosphate granules were bonded to each other while retaining their original shape.

Example 12

Hydroxyapatite powder was compressed in a tablet machine, and then milled in a mortar. The milled powder was further granulated to obtain hydroxyapatite granules having a particle size of 100 to 400 μm. The thus obtained hydroxyapatite granules were distributed on a dish made of alumina so as not to contact each other. The granules were then fired at 1,200° C. for 3 hours. Added to 1 g of the thus obtained fired hydroxyapatite granules was 0.5 g of unfired hydroxyapatite powder having an average particle size of 3 μm, and the mixture was fired at 1,200° C. for 4 hours. It was observed in the fired product that the hydroxyapatite granules were bonded to each other while retaining their original shape.

In this example, a shrinkage of the bonded product at sintering could be diminished more than Example 1, because the previously fired hydroxyapatite granules were used in place of the unfired granules, and then they were bonded to obtain a bonded product.

Example 13

The procedure of Example 12 was repeated to obtain fired hydroxyapatite granules having a particle size of 100 to 400 $\mu$m. Added to 1 g of the thus obtained fired hydroxyapatite granules was 0.5 g of unfired hydroxyapatite powder having an average particle size of 3 $\mu$m and 2 ml of water, in that order, and the mixture was fired at 1,200° C. for 4 hours.

It was observed in the fired product that the hydroxyapatite granules were bonded to each other while retaining their original shape.

In this example, a shrinkage of the bonded product at sintering could be more diminished than Example 1, because the previously fired hydroxyapatite granules were used in place of the unfired granules, and then they were bonded to obtain a bonded product. In addition, good bonding conditions could be obtained for each hydroxyapatite granule, because the fine hydroxyapatite powder was uniformly adhered to the hydroxyapatite granules.

Example 14

Step 1:
The procedure of Example 2 was repeated to obtain unfired porous hydroxyapatite granules having a particle size of 100 to 400 $\mu$m and a porosity of 20%. The thus obtained unfired hydroxyapatite granules were distributed on a dish made of alumina so as not to contact each other. The granules were then fired at 1,200° C. for 3 hours to obtain fired hydroxyapatite granules.

Step 2:
Added to 1 g of the fired hydroxyapatite granules obtained in the above step 1 was 0.5 g of unfired hydroxyapatite powder having an average particle size of 3 $\mu$m, and the mixture was fired at 1,200° C. for 4 hours. It was observed in the fired product that the hydroxyapatite granules were bonded to each other while retaining their original shape. Due to use of the previously fired hydroxyapatite granules, shrinkage of the bonded product at sintering could be diminished to a lower level.

Step 3:
Added to 1 g of the fired hydroxyapatite granules obtained in the above step 1 was 0.5 g of unfired hydroxyapatite powder having an average particle size of 3 $\mu$m and 2 ml of water, in that order, and the mixture was fired at 1,200° C. for 4 hours, after stirring. It was observed in the fired product that the hydroxyapatite granules were bonded to each other while retaining their original shape. Shrinkage of the bonded product at sintering could be diminished to a lower level, and good bonding conditions could be obtained for each hydroxyapatite granule, because the fine hydroxyapatite powder was uniformly adhered to the hydroxyapatite granules.

Example 15

Step 1:
The procedure of Example 3 was repeated to obtain unfired porous tricalcium phosphate granules having a particle size of 100 to 400 $\mu$m and a porosity of 20%. The thus obtained unfired tricalcium phosphate granules were distributed on a dish made of alumina so as not to contact each other. The granules were then fired at 1,200° C. for 3 hours to obtain fired tricalcium phosphate granules.

Step 2:
Added to 1 g of the fired tricalcium phosphate granules obtained in the above step 1 was 0.5 g of unfired tricalcium phosphate powder having an average particle size of 3 $\mu$m, and the mixture was fired at 1,200° C. for 4 hours. It was observed in the fired product that the tricalcium phosphate granules were bonded to each other while retaining their original shape. Due to use of the previously fired tricalcium phosphate granules, shrinkage of the bonded product at sintering could be diminished to a lower level.

Step 3:
To 1 g of the fired tricalcium phosphate granules obtained in the above step 1, added was 0.5 g of unfired tricalcium phosphate powder having an average particle size of 3 $\mu$m and 2 ml of water, in that order, and the mixture was fired at 1,200° C. for 4 hours, after stirring. It was observed in the fired product that the tricalcium phosphate granules bonded to each other while retaining their original shape. Shrinkage of the bonded product at sintering could be diminished to a lower level, and good bonding conditions could be obtained for each tricalcium phosphate granule, because the fine powders were uniformly adhered to the tricalcium phosphate granules.

Example 16

Step 1:
The procedure of Example 4 was repeated to obtain unfired dense hydroxyapatite granules having a particle size of 100 to 400 $\mu$m. The thus obtained unfired hydroxyapatite granules were distributed on a dish made of alumina so as not to contact each other. The granules were then fired at 1,200° C. for 3 hours to obtain fired hydroxyapatite granules.

Step 2:
Added to 1 g of the fired hydroxyapatite granules obtained in the above step 1 was 0.5 g of unfired hydroxyapatite powder having an average particle size of 3 $\mu$m, and the mixture was fired at 1,200° C. for 4 hours. It was observed in the fired product that the hydroxyapatite granules were bonded to each other while retaining their original shape. Due to use of the previously fired hydroxyapatite granules, shrinkage of the bonded product at sintering could be diminished to a lower level.

Step 3:
Added to 1 g of the fired hydroxyapatite granules obtained in the above step 1 was 0.5 g of unfired hydroxyapatite powder having an average particle size of 3 $\mu$m and 2 ml of water, in that order, and the mixture was fired at 1,200° C. for 4 hours, after stirring. It was observed in the fired product that the hydroxyapatite granules bonded to each other while retaining their original shape. Shrinkage of the bonded product at sintering could be diminished to a lower level, and good bonding conditions could be obtained for each hydroxyapatite granule, because the fine powders were uniformly adhered to the hydroxyapatite granules.

Example 17

Step 1:
The procedure of Example 5 was repeated to obtain unfired dense tricalcium phosphate granules having a particle size of 100 to 400 $\mu$m. The thus obtained unfired tricalcium phosphate granules were distributed on a dish made of alumina so as not to contact each other. The granules were then fired at 1,200° C. for 3 hours to obtain fired tricalcium phosphate granules.

Step 2:
Added to 1 g of the fired tricalcium phosphate granules obtained in the above step 1 was 0.5 g of unfired tricalcium phosphate powder having an average particle size of 3 $\mu$m, and the mixture was fired at 1,200° C. for 4 hours. It was observed in the fired product that the tricalcium phosphate granules were bonded to each other while retaining their original shape. Due to use of the previously fired tricalcium phosphate granules, shrinkage of the bonded product at sintering could be diminished to a lower level.

Step 3:

Added to 1 g of the fired tricalcium phosphate granules obtained in the above step 1 was 0.5 g of unfired tricalcium phosphate powder having an average particle size of 3 $\mu$m and 2 ml of water, in that order, and the mixture was fired at 1,200° C. for 4 hours, after stirring. It was observed in the fired product that the tricalcium phosphate granules were bonded to each other while retaining their original shape. Shrinkage of the bonded product at sintering could be diminished to a lower level, and good bonding conditions could be obtained for each tricalcium phosphate granule, because the fine powders were uniformly adhered to the tricalcium phosphate granules.

Comparative Example 6

Hydroxyapatite powder were compressed in a tablet machine, and then milled in a mortar. The milled powder was further granulated to obtain hydroxyapatite granules having a particle size of 100 to 400 $\mu$m. 1 g of the thus obtained hydroxyapatite granules was added to a crucible, and fired at 1,200° C. for 4 hours. The hydroxyapatite granules did not bond to each other.

Comparative Example 7

The unfired hydroxyapatite granules obtained in Comparative Example 6 were distributed on a dish made of alumina so as not to contact each other, and then fired at 1,200° C. for 3 hours. 1 g of the thus obtained fired hydroxyapatite granules was added to a crucible, and fired at 1,200° C. for 4 hours. The hydroxyapatite granules did not bond to each other.

Comparative Example 8

The procedure of Example 2 was repeated to obtain unfired porous hydroxyapatite granules having a particle size of 100 to 400 $\mu$m and a porosity of 20%. The unfired hydroxyapatite granules were distributed on a dish made of alumina so as not to contact each other, and then fired at 1,200° C. for 3 hours. 1 g of the thus obtained fired hydroxyapatite granules was added to a crucible, and fired at 1,200° C. for 4 hours. The hydroxyapatite granules did not bond to each other.

Comparative Example 9

The procedure of Example 3 was repeated to obtain unfired porous tricalcium phosphate granules having a particle size of 100 to 400 $\mu$m and a porosity of 20%. The unfired tricalcium phosphate granules were distributed on a dish made of alumina so as not to contact each other, and then fired at 1,200° C. for 3 hours. 1 g of the thus obtained fired tricalcium phosphate granules was added to a crucible, and fired at 1,200° C. for 4 hours. The tricalcium phosphate granules did not bond to each other.

Comparative Example 10

The procedure of Example 4 was repeated to obtain unfired dense hydroxyapatite granules having a particle size of 100 to 400 $\mu$m. The unfired hydroxyapatite granules were distributed on a dish made of alumina so as not to contact each other, and then fired at 1,200° C. for 3 hours. 1 g of the thus obtained fired hydroxyapatite granules was added to a crucible, and fired at 1,200° C. for 4 hours. The hydroxyapatite granules did not bond to each other.

Comparative Example 11

The procedure of Example 5 was repeated to obtain unfired dense tricalcium phosphate granules having a particle size of 100 to 400 $\mu$m. The unfired tricalcium phosphate granules were distributed on a dish made of alumina so as not to contact each other, and then fired at 1,200° C. for 3 hours. 1 g of the thus obtained fired tricalcium phosphate granules was added to a crucible, and fired at 1,200° C. for 4 hours. The tricalcium phosphate granules did not bond to each other.

Example 18

Unfired porous hydroxyapatite granules were milled to obtain granules having a particle size of 100 to 400 $\mu$m. Added to 1 g of the milled hydroxyapatite granules was 0.2 g of fine hydroxyapatite powder having an average particle size of 3 $\mu$m and 1 g of an aqueous 1 wt. % solution of methyl cellulose, and the mixture was charged in a container. The mixture was left to stand at 80° C. for 24 hours under closed conditions to cause gelation. After completion of the gelation, the obtained gel was dried at 80° C. for 12 hours in an open mold, and further dried (at 80° C.) for 24 hours after removal of the dried product from the container. The dried product was fired, and then fired at 1,200° C. for 4 hours. The hydroxyapatite granules were bonded to each other while retaining their original shape.

Example 19

Unfired dense hydroxyapatite granules were milled to obtain granules having a particle size of 100 to 400 $\mu$m. Added to 1 g of the milled hydroxyapatite granules was 0.2 g of fine hydroxyapatite powder having an average particle size of 3 $\mu$m and 1 g of an aqueous 1 wt. % solution of methyl cellulose, and the mixture was charged in a container. The mixture was left to stand at 80° C. for 24 hours under the closed conditions to cause gelation. After completion of gelation, the obtained gel was dried at 80° C. for 12 hours in an open mold, and further dried (at 80° C.) for 24 hours after removal of the dried product from the container. The dried product was fired at 1,200° C. for 4 hours. The hydroxyapatite granules were bonded to each other while retaining their original shape.

Comparative Example 12

Unfired porous hydroxyapatite granules were milled to obtain granules having a particle size of 100 to 400 $\mu$m. Added to 1 g of the milled hydroxyapatite granules was 0.2 g of fine hydroxyapatite powder having an average particle size of 3 $\mu$m and 1 g of water, and the mixture was charged in a container. The mixture was dried at 80° C. for 12 hours in an open mold, however, the dried product could not be removed from the container, because, upon evaporation of water during drying, it was again separated into the hydroxyapatite granules and the fine hydroxyapatite powder as the starting materials. That is, this comparative example indicates that a binding agent for bonding the hydroxyapatite granules with the fine hydroxyapatite powder is required to obtain a strength sufficient for the molding process.

Example 20

Unfired porous tricalcium phosphate granules were milled to obtain granules having a particle size of 100 to 400 $\mu$m.

Added to 1 g of the milled tricalcium phosphate granules was 0.2 g of fine hydroxyapatite powder having an average particle size of 3 μm and 1 g of an aqueous 1% solution of methyl cellulose, and the mixture was charged in a container. The mixture was left to stand at 80° C. for 24 hours under closed conditions to cause gelation. After completion of the gelation, the obtained gel was dried at 80° C. for 12 hours in an open mold, and further dried (at 80° C.) for 24 hours after removal of the dried product from the container. The dried product was fired at 1,200° C. for 4 hours. The tricalcium phosphate granules bonded to each other while retaining their original shape.

Example 21

Unfired porous hydroxyapatite granules were milled to obtain granules having a particle size of 600 to 1,000 μm, and then fired at 1,200° C. for 4 hours. Added to 1 g of the fired hydroxyapatite granules was 0.2 g of fine hydroxyapatite powder having an average particle size of 3 μm and 1 g of an aqueous 1% solution of methyl cellulose, and the mixture was charged in a container. The mixture was left to stand at 80° C. for 24 hours under closed conditions to cause gelation. After completion of the gelation, the obtained gel was dried at 80° C. for 12 hours in an open mold, and further dried (at 80° C.) for 24 hours after removal of the dried product from the container. The dried product was fired at 1,200° C. for 4 hours. The hydroxyapatite granules bonded to each other while retaining their original shape.

Example 22

Hydroxyapatite powder was compressed in a tablet machine, and then milled in a mortar. The milled powder was further subjected to a particle size controlling process to obtain hydroxyapatite granules having a particle size of 100 to 400 μm. About 1 g of the thus obtained hydroxyapatite granules and 0.5 g of unfired hydroxyapatite powder having an average particle size of 3 μm were mixed with 5 ml of ethanol, and then fired at 1,200° C. for 4 hours. The hydroxyapatite granules were bonded to each other while retaining their original shape.

As can be appreciated from the above descriptions, the prosthetic bone material according to the present invention includes a bonded product produced by bonding granules of calcium phosphate compound to each other, while retaining an original shape of the granules, and therefore can be handled as a block product. Further, since the present prosthetic bone material can be easily disintegrated into granules with pushing pressure of the human hand (1–50 kg/cm$^2$), or the like, during an operation, it becomes possible to prevent undesirable scattering of the granules around the operation site, and also to easily shape the prosthetic material in conformity with the configuration of the bone-lacking portion to be repaired. Furthermore, in the production process of the prosthetic bone material according to the present invention, when the granules of calcium phosphate compound and particulates of calcium phosphate compound acting as a binder are mixed along with an aqueous solution of a binding agent, it becomes possible to remarkably increase the mechanical strength of the resulting dried product, enabling the removal of the dried product from a mold, prior to firing, thereby notably improving moldability of the product.

Although the invention has been described with reference to particular means, materials and embodiments, it is to be understood that the invention is not limited to the particulars disclosed and extends to all equivalents within the scope of the claims.

What is claimed is:

1. A prosthetic bone material comprising:
    a bonded and sintered product formed by mixing and bonding unfired granules of calcium phosphate compound having a particle size of at least about 100 μm with particulates of unfired calcium phosphate compound having a particle size of about 1 to 40 μm, said granules being bonded to each other by said particulates, and said granules comprising a size and shape that is maintained or substantially maintained after formation of the bonded and sintered product as well as when the bonded and sintered product is disintegrated.

2. A prosthetic bone material according to claim 1, in which said granules of calcium phosphate compound having a particle size of at least 100 μm and said particulates of calcium phosphate compound having a particle size of about 1 to 40 μm are contained in a ratio by weight of 1:0.1 to 1:1.

3. A process for the production of a prosthetic bone material which comprises:
    mixing unfired granules of calcium phosphate compound having a particle size of at least about 100 μm with unfired particulates of calcium phosphate compound having a particle size of about 1 to 40 μm, and
    firing the mixture at a temperature of about 800 to 1,200° C.

4. A process for the production of a prosthetic bone material according to claim 3, in which said granules of calcium phosphate compound having a particle size of at least 100 μm and said particulates of calcium phosphate compound having a particle size of about 1 to 40 μm are mixed in a ratio by weight of 1:0.1 to 1:1.

5. A process for the production of a prosthetic bone material which comprises:
    mixing granules of calcium phosphate compound having a particle size of at least 100 μm with particulates of calcium phosphate compound having a particle size of about 1 to 40 μm,
    adding to the mixture an aqueous solution of at least one of a dispersing agent and a binding agent capable of being dissipated during firing, and, after molding and drying,
    firing the molded and dried product at a temperature of about 800 to 1,200° C.

6. A process for the production of a prosthetic bone material according to claim 5, in which said binding agent is selected from group consisting of cellulose derivatives, polysaccharides and synthetic polymers.

7. A prosthetic bone material according to claim 1, wherein said granules comprise a size and shape that is maintained after formation of the bonded and sintered product as well as when the bonded and sintered product is disintegrated.

8. A prosthetic bone material according to claim 1, wherein said bonded and sintered product is capable of disintegrating under pressure applied by a human finger ranging from 1 kg/cm$^2$ to about 50 kg/cm$^2$.

9. A prosthetic bone material produced by the process of claim 3.

10. A prosthetic bone material produced by the process of claim 4.

11. A prosthetic bone material produced by the process of claim 5.

12. A prosthetic bone material produced by the process of claim 6.

* * * * *